US009976979B2

(12) United States Patent
Okazaki et al.

(10) Patent No.: US 9,976,979 B2
(45) Date of Patent: May 22, 2018

(54) GAS SENSOR ELEMENT, GAS SENSOR, AND METHOD OF MANUFACTURING GAS SENSOR ELEMENT

(71) Applicant: NGK SPARK PLUG CO., LTD., Nagoya-shi, Aichi (JP)

(72) Inventors: Satoshi Okazaki, Kasugai (JP); Akinori Kojima, Ichinomiya (JP); Masaki Mizutani, Aichi (JP); Nobuo Furuta, Kasugai (JP); Ai Igarashi, Konan (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 0 days. days.

(21) Appl. No.: 14/862,209

(22) Filed: Sep. 23, 2015

(65) Prior Publication Data

US 2016/0091456 A1    Mar. 31, 2016

(30) Foreign Application Priority Data

Sep. 25, 2014  (JP) ................................. 2014-195520
Jun. 19, 2015  (JP) ................................. 2015-123522
Jun. 19, 2015  (JP) ................................. 2015-123853

(51) Int. Cl.
  *G01N 27/407*  (2006.01)
  *B05D 3/06*  (2006.01)
  (Continued)

(52) U.S. Cl.
  CPC ......... *G01N 27/4073* (2013.01); *B05D 3/002* (2013.01); *B05D 3/0254* (2013.01); *B05D 3/06* (2013.01)

(58) Field of Classification Search
  CPC ........... G01N 27/406; G01N 27/407–27/4078; G01N 27/409; G01N 27/41
  See application file for complete search history.

(56) References Cited

U.S. PATENT DOCUMENTS

| 2005/0189222 A1 | 9/2005 | Tsuzuki et al. |
| 2012/0111726 A1* | 5/2012 | Couto Petri ....... G01N 27/4075 204/424 |
| 2013/0032480 A1* | 2/2013 | Ito ........................ G01N 27/406 204/424 |

FOREIGN PATENT DOCUMENTS

| JP | 2005271578 A | 10/2005 |
| JP | 2007-278941 A | 10/2007 |
| JP | 2013-007642 A | 1/2013 |

OTHER PUBLICATIONS

Communication dated Jan. 9, 2018 from the Japanese Patent Office in counterpart Japanese application No. 2015-123853.

* cited by examiner

*Primary Examiner* — Bethany L Martin
(74) *Attorney, Agent, or Firm* — Sughrue Mion, PLLC

(57) ABSTRACT

A gas sensor element (10) includes a first composite ceramic layer (111) having a plate-shaped first surrounding portion (112) formed of an insulating ceramic and including a through hole inner-perimetric-surface (115) which defines a through hole (112h), and a plate-shaped first electrolyte portion (121) formed of a solid electrolyte ceramic, disposed in the through hole (112h), and including an electrolyte outer-perimetric-surface (125) in contact with the through hole inner-perimetric-surface (115). The electrolyte outer-perimetric-surface (125) of the first electrolyte portion (121) is sloped toward an exterior of the first electrolyte portion (121) as it approaches one side DT1. The through hole inner-perimetric-surface (115) and the electrolyte outer-perimetric-surface 125 are in close contact with each other along their entire perimeters.

7 Claims, 8 Drawing Sheets

(51) Int. Cl.
*B05D 3/00* (2006.01)
*B05D 3/02* (2006.01)

GAS SENSOR ELEMENT, GAS SENSOR, AND METHOD OF MANUFACTURING GAS SENSOR ELEMENT

BACKGROUND OF THE INVENTION

1. Field of the Invention

The present invention relates to a gas sensor element for detecting a gas to be measured, a gas sensor having the gas sensor element, and a method of manufacturing the gas sensor element.

2. Description of the Related Art

Patent Document 1, for example, discloses a gas sensor element having a layer (a composite ceramic layer, described below) configured such that a solid electrolyte body (an electrolyte portion, described below) is disposed in a through hole formed in an insulating member (a surrounding portion, described below).

[Patent Document 1] Japanese Patent Application Laid-Open (kokai) No. 2007-278941

3. Problems to be Solved by the Invention

In the gas sensor element of Patent Document 1, the outer perimetric surface (an electrolyte outer-perimetric-surface, described below) of the solid electrolyte body (electrolyte portion) is in contact with the inner perimetric surface (a through hole inner-perimetric-surface, described below) of the through hole which is substantially perpendicular to the surface of the insulating member (surrounding portion). Accordingly, since the contact length along the thickness direction between the electrolyte outer-perimetric-surface of the electrolyte portion and the through hole inner-perimetric-surface of the surrounding portion is short, in the course of manufacturing the gas sensor element, a sufficient contact length along the thickness direction fails to be secured between the electrolyte outer-perimetric-surface of the electrolyte portion and the through hole inner-perimetric-surface of the surrounding portion. This potentially results in the occurrence of a problem in which the opposite main surfaces of the electrolyte portion communicate with each other through a gap formed between the electrolyte outer-perimetric-surface and the through hole inner-perimetric-surface.

SUMMARY OF THE INVENTION

The present invention has been made in view of the above problem, and an object thereof is to provide a gas sensor element of high reliability by restraining a problem resulting from the formation of a gap between the electrolyte portion and the surrounding portion, as well as a gas sensor including the gas sensor element and a method of manufacturing the gas sensor element.

The above object of the present invention has been achieved, in a first aspect, by providing (1) a gas sensor element comprising a first composite ceramic layer. The first composite ceramic layer has a plate-shaped first electrolyte portion formed of a solid electrolyte ceramic and including an electrolyte outer-perimetric-surface, and a plate-shaped first surrounding portion formed of an insulating ceramic or a mixture of an insulating ceramic and the solid electrolyte ceramic and including a through hole inner-perimetric-surface which defines a through hole extending therethrough in a thickness direction of the gas sensor element. The first electrolyte portion is disposed in the through hole, and the electrolyte outer-perimetric-surface of the first electrolyte portion is in contact with the through hole inner-perimetric-surface of the first surrounding portion. Mutually facing mating surfaces of the electrolyte outer-perimetric-surface of the first electrolyte portion and the through hole inner-perimetric-surface of the first surrounding portion, respectively, are sloped toward an exterior of the first electrolyte portion as they approach one side with respect to the thickness direction and are entirely in close contact with each other.

In the above-described gas sensor element (1), since the mating surface of the electrolyte outer-perimetric-surface of the first electrolyte portion and the mating surface of the through hole inner-perimetric-surface of the first surrounding portion are sloped such that the positions of the mating surfaces change outwardly while moving toward one side with respect to the thickness direction, the contact length along the thickness direction between the mating surface of the first electrolyte portion and the mating surface of the first surrounding portion can be increased. Furthermore, the mating surfaces of the through hole inner-perimetric-surface and the electrolyte outer-perimetric-surface are entirely in close contact with each other. Thus, the formation of a communication gap between opposing main surfaces of the first electrolyte portion can be restrained between the first electrolyte portion and the first surrounding portion. Consequently, the gas sensor element can be free from deterioration in accuracy, which could otherwise result from the flow of gas through the gap. Therefore, the gas sensor element can provide high reliability.

Notably, in one mode of the first composite ceramic layer, the entire electrolyte outer-perimetric-surface of the first electrolyte portion and the entire through hole inner-perimetric-surface of the first surrounding portion may serve as the respective mating surfaces. In another mode of the first composite ceramic layer, because of a difference in thickness or disposition between the first electrolyte portion and the first surrounding portion, the electrolyte outer-perimetric-surface of the first electrolyte portion or the through hole inner-perimetric-surface of the first surrounding portion may include an unmated surface on one side and/or the other side along the thickness direction with respect to the mating surface.

Preferably, the electrolyte outer-perimetric-surface is inclined or "sloped" such that, in a vertical section of the first electrolyte portion taken along the thickness direction, an angle θ (acute angle (0° to 90°) between the main surface on one side of the first electrolyte portion and the mating surface (slope) of the electrolyte outer-perimetric-surface satisfies the relation 45°≤θ≤80°, more preferably 55°≤θ≤75°. If the angle θ between the main surface on one side of the first electrolyte portion and the mating surface (slope) of the electrolyte outer-perimetric-surface exceeds 80°, the mating surface is sloped, but is close to a vertical surface, resulting in a failure to secure a sufficient contact length. If the angle θ between the main surface on one side of the first electrolyte portion and the mating surface (slope) of the electrolyte outer-perimetric-surface is less than 45°, a difficulty is encountered in securing a sufficient area of the main surface on the other side of the first electrolyte portion, so that the size of an electrode provided on the main surface on the other side is reduced, resulting in a reduction in sensor output.

In addition to an insulating ceramic (e.g., alumina), a mixture of an insulating ceramic and a solid electrolyte ceramic (e.g., a mixed ceramic of alumina and zirconia) can be used to form the first surrounding portion of the first composite ceramic layer.

In a preferred embodiment (2) of the gas sensor element (1), the first electrolyte portion is formed by firing an electrolyte sheet member which contains the solid electrolyte ceramic and whose sheet member outer-perimetric-surface is sloped toward an exterior of the sheet member as it approaches the one side with respect to a sheet thickness direction, and the first surrounding portion is formed by firing a layer of ceramic paste which is in contact with the sheet member outer-perimetric-surface of the electrolyte sheet member and contains the insulating ceramic or a mixture of the insulating ceramic and the solid electrolyte ceramic.

In formation of the above-mentioned gas sensor element (2), the first electrolyte portion is formed by firing the electrolyte sheet member, and the first surrounding portion is formed by firing a layer of insulating paste. Furthermore, before firing, the layer of insulating paste is in contact with the sheet member outer-perimetric-surface of the electrolyte sheet member. Thus, since firing is performed while the slope of the sheet member outer-perimetric-surface is maintained, a mating surface of the electrolyte outer-perimetric-surface of the first electrolyte portion can be reliably sloped as mentioned above. Furthermore, the layer of insulating paste is in close contact with the sheet member outer-perimetric-surface which is to become the electrolyte outer-perimetric-surface. Therefore, the gas sensor element can be configured such that the mating surface of the electrolyte outer-perimetric-surface and the mating surface of the through hole inner-perimetric-surface can be entirely in close contact with each other in a reliable manner.

Also, in addition to an insulating ceramic (e.g., alumina), a mixture of an insulating ceramic and a solid electrolyte ceramic (e.g., a mixed ceramic of alumina and zirconia) can be used to form the ceramic paste.

In another preferred embodiment (3), the above gas sensor element (1) or (2) further comprises a heater located on the one side with respect to the thickness direction in relation to the first composite ceramic layer and adapted to heat the first electrolyte portion.

In the gas sensor element (3), the heater is disposed on the one side with respect to the first electrolyte portion having the mating surface (slope) which is sloped such that its position changes outwardly while moving toward the one side with respect to the thickness direction. That is, the configuration in which the first electrolyte portion, whose sectional area increases while moving toward the one side, is heated by the heater from the one side with respect to the first electrolyte portion, facilitates heating of the first electrolyte portion. Consequently, the temperature of the first electrolyte portion can be increased and the first electrolyte portion can be activated more quickly.

In yet another preferred embodiment (4), the above gas sensor element (3) further comprises a second composite ceramic layer disposed between the first composite ceramic layer and the heater, and is configured as follows. The second composite ceramic layer has a plate-shaped second electrolyte portion formed of the solid electrolyte ceramic and including a second electrolyte outer-perimetric-surface, and a plate-shaped second surrounding portion formed of the insulating ceramic or a mixture of the insulating ceramic and the solid electrolyte ceramic, including a second through hole inner-perimetric-surface which defines a second through hole extending therethrough in the thickness direction of the gas sensor element, and having a thermal conductivity higher than that of the second electrolyte portion. The second electrolyte portion is disposed in the second through hole, and the second electrolyte outer-perimetric-surface of the second electrolyte portion is in contact with the second through hole inner-perimetric-surface of the second surrounding portion. The second electrolyte portion is located away from the first electrolyte portion of the first composite ceramic layer to form therebetween a measuring chamber into which a gas to be measured is introduced. Mutually facing second mating surfaces of the second electrolyte outer-perimetric-surface of the second electrolyte portion and the second through hole inner-perimetric-surface of the second surrounding portion, respectively, are sloped toward an interior of the second electrolyte portion as they approach one side with respect to the thickness direction and are entirely in close contact with each other.

The gas sensor element (4) further comprises the second composite ceramic layer in addition to the first composite ceramic layer. The measuring chamber is formed between the second electrolyte portion of the second composite ceramic layer and the first electrolyte portion of the first composite ceramic layer. Also, the second surrounding portion has a higher thermal conductivity than the second electrolyte portion. Furthermore, in contrast to the mating surface of the first composite ceramic layer, the second mating surface of the second composite ceramic layer is sloped such that its position changes inwardly while moving toward the one side. That is, in the second composite layer, the second surrounding portion, which has a higher thermal conductivity than the second electrolyte portion, has a greater area on the one side (i.e., on the heater side) than on the other side.

In the gas sensor element (4), since the second composite ceramic layer intervenes between the first composite ceramic layer and the heater, and the measuring chamber is present therebetween, heat generated by the heater is less likely to reach the first electrolyte portion of the first composite ceramic layer as compared with the second electrolyte portion of the second composite ceramic layer. Accordingly, the temperature of the first electrolyte portion of the first composite ceramic layer is less likely to increase. However, in this gas sensor element, the second surrounding portion can receive heat generated by the heater in a greater amount from the surface facing the one side and having has a relatively large area of the second surrounding portion having a relatively high thermal conductivity, whereby the heat can be efficiently transmitted to the first composite ceramic layer. Thus, as compared with the case where the second mating surface is parallel to the thickness direction or is sloped such that its position changes outwardly while moving toward the one side, the first electrolyte portion of the first composite ceramic layer can be more efficiently heated to increase its temperature.

In a second aspect (5) the present invention provides a gas sensor comprising any one of the gas sensor elements (1) to (4) above.

Since the above-mentioned gas sensor (5) comprises the above-mentioned gas sensor element, the gas sensor can provide high reliability by restraining a problem resulting from formation of a gap between the first electrolyte portion and the first surrounding portion.

In a third aspect (6), the present invention provides a method of manufacturing a gas sensor element which comprises a first composite ceramic layer having a plate-shaped first electrolyte portion formed of a solid electrolyte ceramic and including an electrolyte outer-perimetric-surface, and a plate-shaped first surrounding portion formed of an insulating ceramic or a mixture of an insulating ceramic and the solid electrolyte ceramic and including a through hole inner-perimetric-surface that defines a through hole extending therethrough in a thickness direction of the gas sensor element, and in which the first electrolyte portion is disposed in the through hole, the electrolyte outer-perimetric-surface of the first electrolyte portion is in contact with the through hole inner-perimetric-surface of the first surrounding portion, and mutually facing mating surfaces of the electrolyte outer-perimetric-surface of the first electrolyte portion and the through hole inner-perimetric-surface of the first surrounding portion, respectively, are sloped toward an exterior of the first electrolyte portion as they approach one side with respect to the thickness direction and are entirely in close contact with each other. The method comprises a composite layer forming step of forming a green composite ceramic layer by disposing a layer of ceramic paste which contains the insulating ceramic or a mixture of the insulating ceramic and the solid electrolyte ceramic, around an electrolyte sheet member formed of a green sheet which contains the solid electrolyte ceramic and having a sheet member outer-perimetric-surface, so that the layer of ceramic paste comes into contact with the sheet member outer-perimetric-surface, followed by drying, the sheet member outer-perimetric-surface being sloped toward an exterior of the sheet member as it approaches one side with respect to a sheet thickness direction; and a firing step of firing the green composite ceramic layer to form the first composite ceramic layer having the first electrolyte portion and the first surrounding portion.

According to the above-mentioned method (6) of manufacturing a gas sensor element, in the composite layer forming step, a layer of insulating plate is disposed around the electrolyte sheet member in contact with the sloped sheet member outer-perimetric-surface. Accordingly, the layer of insulating paste can be reliably brought in close contact with the sheet member outer-perimetric-surface with a large contact area. Thus, a gas sensor element can be manufactured which provides high reliability by preventing the formation, after firing, of a gap between the mating surfaces of the electrolyte outer-perimetric-surface of the first electrolyte portion and the through hole inner-perimetric-surface of the first surrounding portion.

The electrolyte sheet member is, for example, punched out from an electrolyte sheet using a punching die or cut out from the electrolyte sheet using an energy beam such as a laser beam or a cutting blade.

Preferably, the sheet member outer-perimetric-surface is sloped such that its position changes outwardly while moving toward the one side with respect to a sheet thickness direction such that, in a vertical section of the electrolyte sheet member taken along the sheet thickness direction, an angle $\theta s$ between the main surface of the electrolyte sheet member and the sheet member outer-perimetric-surface (slope) satisfies the relation $45°\leq\theta s\leq 80°$, more preferably $55°\leq\theta s\leq 75°$. If the angle $\theta s$ between the main surface of the electrolyte sheet member and the sheet member outer-perimetric-surface exceeds 80°, the sheet member outer-perimetric-surface is sloped, but is close to a vertical surface, resulting in a failure to secure a sufficient contact length in relation to the surrounding layer of ceramic paste. If the angle $\theta s$ between the main surface of the electrolyte sheet member and the sheet member outer-perimetric-surface is less than 45°, after firing, it is difficult to secure a sufficient area of the main surface on the other side of the first electrolyte portion, so that the size of an electrode provided on the main surface on the other side is reduced, resulting in a reduction in sensor output.

In a preferred embodiment (7), the above method of manufacturing a gas sensor element (6) further comprises a cutting-out step of cutting out, prior to the composite layer forming step, the electrolyte sheet member from the green sheet by directing a conically converging laser beam from a CW laser onto the green sheet and moving the laser beam in a planar direction of the green sheet.

Since the above-mentioned method (7) of manufacturing a gas sensor element further comprises the cutting-out step, an electrolyte sheet member whose cut surface (sheet member outer-perimetric-surface) is sloped can be reliably formed. Therefore, the gas sensor element can be manufactured by reliably using the electrolyte sheet member whose sheet member outer-perimetric-surface is sloped as described above.

DESCRIPTION OF REFERENCE NUMERALS

Figure 1:
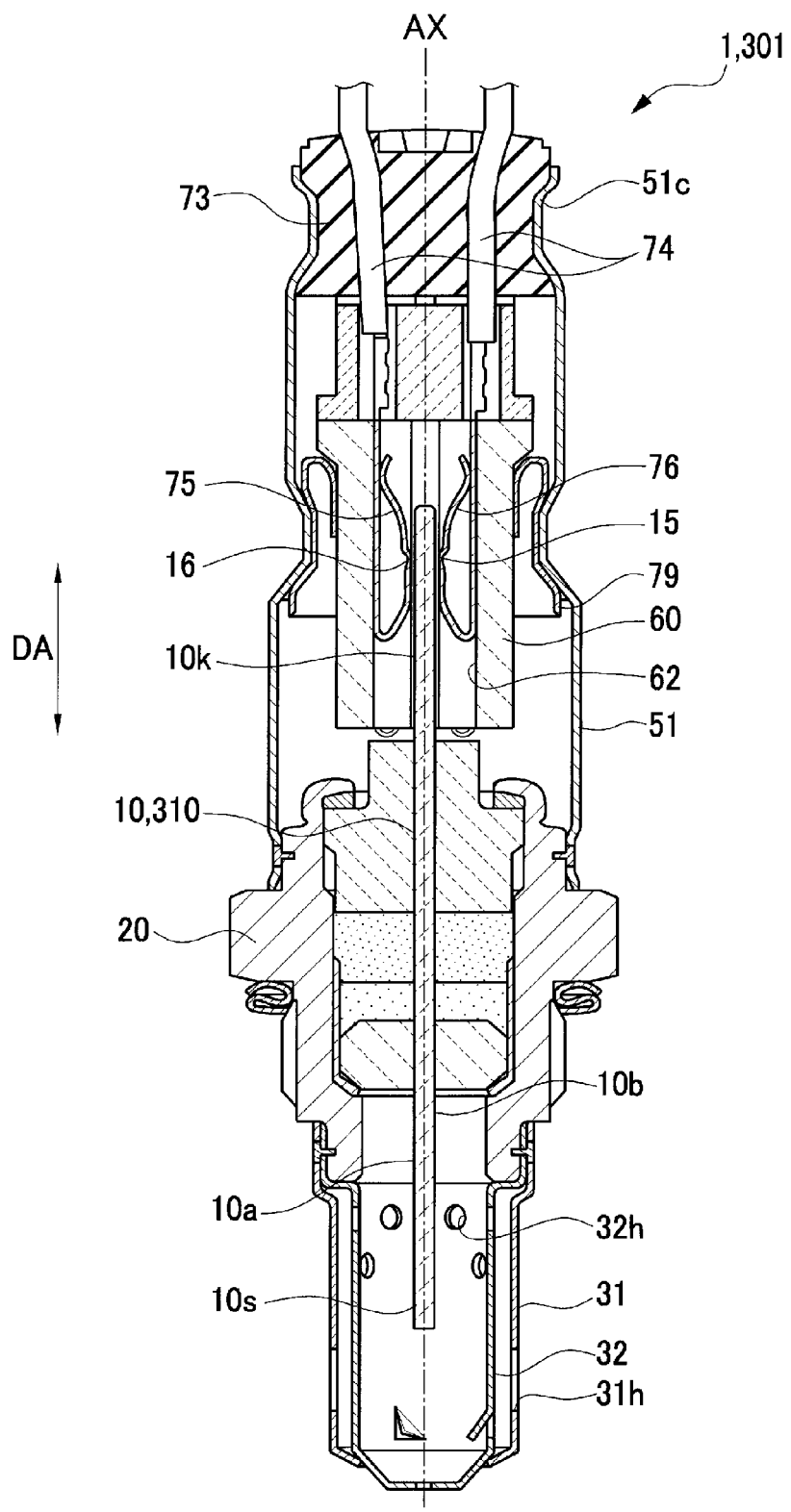
FIG. 1 is a longitudinal sectional view of a gas sensor including a gas sensor element according to an embodiment or modified embodiment of the present invention.

Reference numerals used to identify various features in the drawings include the following:
1, 301: gas sensor
10, 310: gas sensor element
111: first composite layer (composite ceramic layer)
112: first surrounding portion (surrounding portion)
112$h$: through hole
115: through hole inner-perimetric-surface
115$k$: mating surface (of through hole inner-perimetric-surface)
121: first electrolyte portion (electrolyte portion)
125: electrolyte outer-perimetric-surface
125$k$: mating surface (of electrolyte outer-perimetric-surface)
131, 331: second composite layer (second composite ceramic layer)
132, 332: second surrounding portion
132$h$, 332$h$: through hole
332$s$: one surface (of second surrounding portion) (surface of second surrounding portion facing one side with respect to thickness direction)
332$r$: the other surface (of second surrounding portion)

135, 335: second through hole inner-perimetric-surface
135k, 335k: second mating surface (mating surface) (of second through hole inner-perimetric-surface)
141, 341: second electrolyte portion
145, 345: second electrolyte outer-perimetric-surface
145k, 345k: second mating surface (mating surface) (of second electrolyte outer-perimetric-surface)
181: heater
SP: measuring chamber
221: green first composite layer (green composite ceramic layer)
212: insulating paste layer (layer of insulating paste)
221: electrolyte sheet member
221B: electrolyte sheet (green sheet)
225: sheet member outer-perimetric-surface
DT: thickness direction
DT1: one side (with respect to thickness direction)
DX: first direction (planar direction of electrolyte sheet)
DY: second direction (planar direction of electrolyte sheet)
DZ: sheet thickness direction
DZ1: one side (with respect to sheet thickness direction)
LB: laser beam

DETAILED DESCRIPTION OF THE PREFERRED EMBODIMENTS

Next, the present invention will be described in greater detail with reference to the drawings. However, the present invention should not be construed as being limited thereto.

Embodiment

Figure 2:
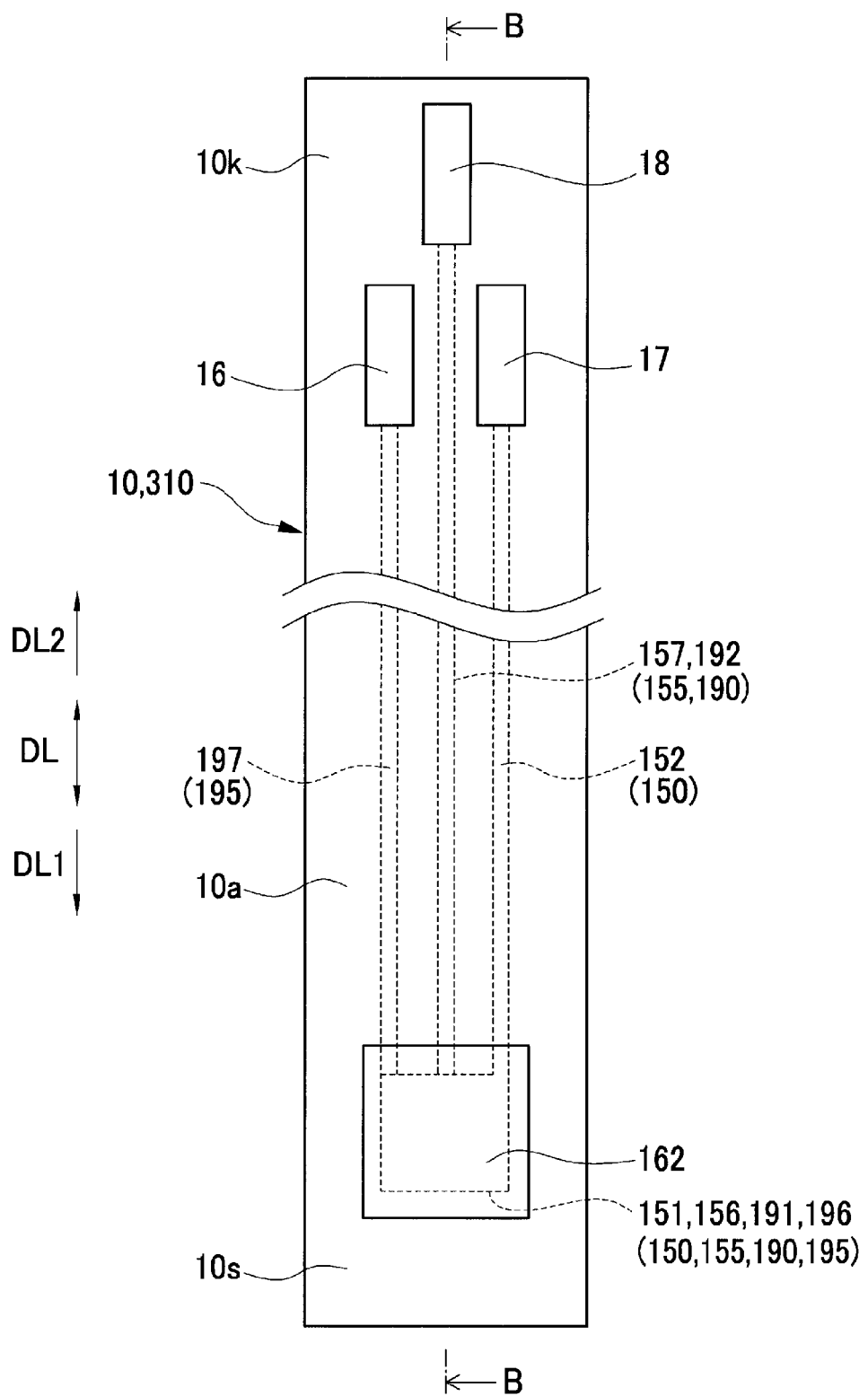
FIG. 2 is a plan view of the gas sensor element according to the embodiment or modified embodiment.
Figure 3:
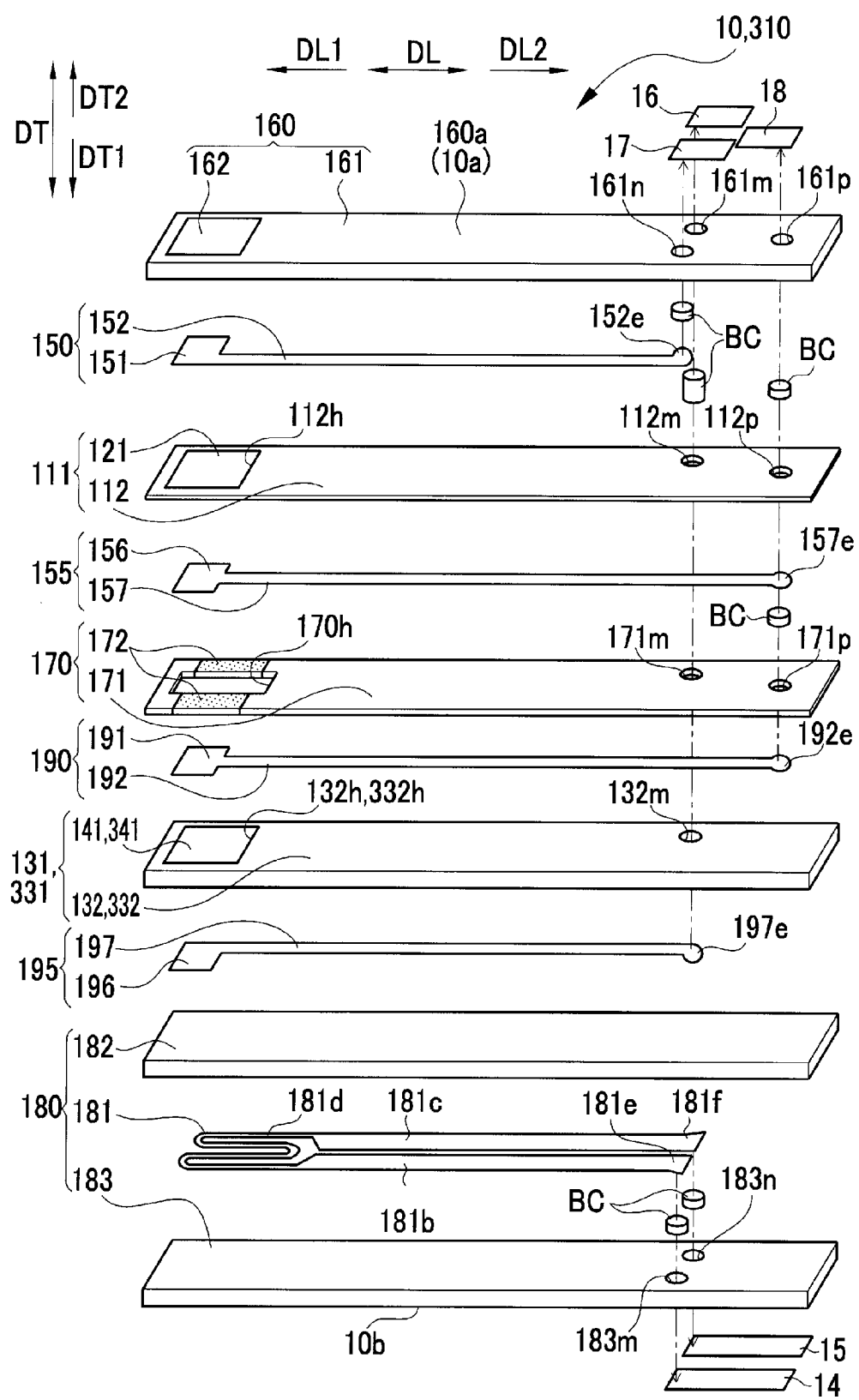
FIG. 3 is an exploded perspective view (schematic view) of the gas sensor element according to the embodiment or modified embodiment.
Figure 4:
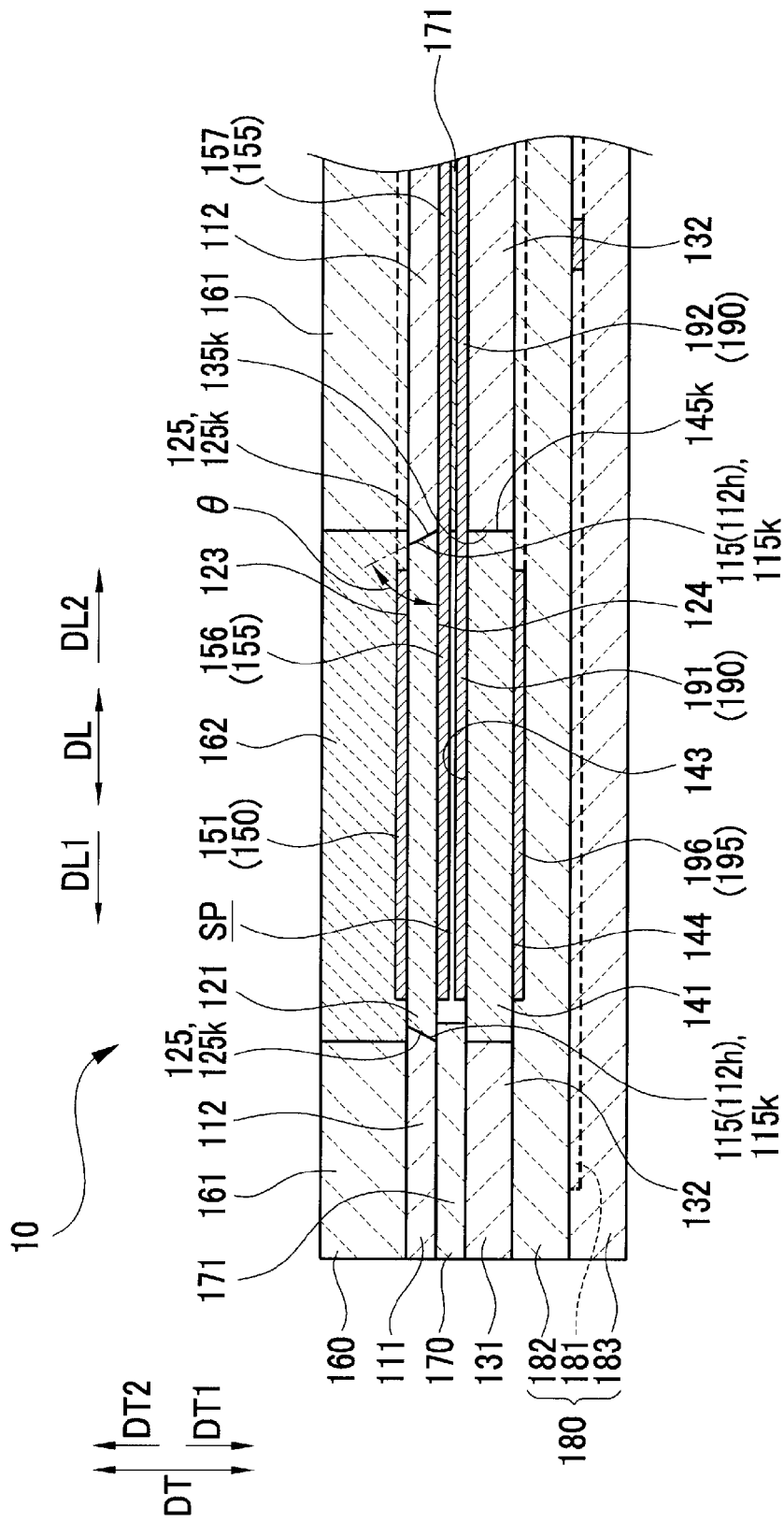
FIG. 4 is an explanatory longitudinal sectional view showing the structure of the gas sensor element according to the embodiment.

First, a gas sensor 1 having a gas sensor element 10 according to an embodiment of the present invention will be described. FIG. 1 is a longitudinal sectional view of the gas sensor 1 according to the embodiment taken along an axial line AX. FIG. 2 is a plan view of the gas sensor element 10 according to the embodiment. FIG. 3 is an exploded perspective view of the gas sensor element 10. FIG. 4 is an explanatory longitudinal sectional view corresponding to a sectional view taken along line B-B of FIG. 2 and shows the internal structure of the gas sensor element 10.

The gas sensor 1 is an oxygen sensor (see FIG. 1) adopted for attaching to an exhaust pipe (not shown) of an internal combustion engine. The gas sensor 1 includes the rectangular plate-like gas sensor element 10 for detecting the oxygen concentration of exhaust gas, which is the gas to be measured, and a tubular metallic shell 20 for holding the gas sensor element 10 therein. An outer protector 31 and an inner protector 32 are disposed on the forward side (lower side in FIG. 1) of the metallic shell 20 with respect to an axial direction DA along the axial line AX, and an outer tube 51 is disposed on the rear side (upper side in FIG. 1) with respect to the axial direction DA. The gas sensor 1 further includes a separator 60 disposed within the outer tube 51 and adapted to hold the gas sensor element 10, and five terminal members 75, 75, 76, 76, and 76 disposed between the separator 60 and the gas sensor element 10 (see FIG. 1). The five terminal members 75, 75, 76, 76, and 76 are elastically in contact with corresponding pads 14, 15, 16, 17, and 18 so as to be electrically connected thereto.

The metallic shell 20 holds the gas sensor element 10 so that a forward end portion 10s of the gas sensor element 10 protrudes from the forward end of the metallic shell 20 (downward in FIG. 1) along the axial direction DA, and a rear end portion 10k of the gas sensor element 10 protrudes from the rearward end of the metallic shell 20 (upward in FIG. 1) along the axial direction DA. The outer protector 31 and the inner protector 32 made of metal cover the forward end portion 10s of the gas sensor element 10. The outer protector 31 and the inner protector 32 have a plurality of holes 31h and 32h, respectively. The gas to be measured is introduced through the holes 31h and 32h from outside the outer protector 31 into a surrounding space around the forward end portion 10s of the gas sensor element 10 disposed inside the inner protector 32.

The outer tube 51 is fitted to a rear end portion of the metallic shell 20 from the rear side with respect to the axial direction DA. The outer tube 51 holds the separator 60 therein by means of a holding member 79, and the separator 60 holds the five terminal members 75 and 76 provided respectively at forward ends of five lead wires 74 so that the terminal members 75 and 76 are separated from one another. The separator 60 has an insertion hole 62 extending therethrough and adapted to receive the rear end portion 10k of the gas sensor element 10 (see FIG. 1).

A rear end opening portion (upper end opening portion in FIG. 1) 51c of the outer tube 51 is closed with a grommet 73 through which the five lead wires 74 extend.

The gas sensor element 10 assumes a rectangular plate-like form and is disposed within the gas sensor 1 with its center line coinciding with the axial line AX (see FIG. 1). A longitudinal direction DL of the gas sensor element 10 is in parallel with the axial direction DA along the axial line AX, and a forward side DL1 with respect to the longitudinal direction DL corresponds to the aforementioned forward side with respect to the axial direction DA. Also, a rear side DL2 with respect to the longitudinal direction DL corresponds to the aforementioned rear side with respect to the axial direction DA.

The gas sensor element 10 has three sensor pads 16, 17, and 18 formed on a first element main surface 10a facing the other side DT2 (upper side in FIGS. 3 and 4) with respect to a thickness direction DT, at the rear end portion 10k. Also, the gas sensor element 10 has two heater pads 14 and 15 formed on a second element main surface 10b facing one side DT1 (lower side in FIGS. 3 and 4) with respect to the thickness direction DT, at the rear end portion 10k. The heater pads 14 and 15 are electrically connected to a heater 181, described below, within the gas sensor element 10. Also, within the gas sensor element 10, the sensor pad 16 is electrically connected to a fourth conductor layer 195, described below; the sensor pad 17 is electrically connected to a first conductor layer 150, described below; and the sensor pad 18 is electrically connected to a second conductor layer 155 and a third conductor layer 190, described below.

The gas sensor element 10 is composed of a plurality of ceramic layers and conductor layers laminated together in the thickness direction DT. Specifically, as shown in FIGS. 3 and 4, a heater layer 180, the fourth conductor layer 195, a second composite layer 131, the third conductor layer 190, an insulating layer 170, the second conductor layer 155, a first composite layer 111, the first conductor layer 150, and a protection layer 160 are sequentially laminated together from the one side DT1.

Among these layers, the second composite layer 131 includes a plate-like second surrounding portion 132 formed of an insulating ceramic (alumina ceramic) and having a through hole 132h which extends therethrough in the thickness direction DT and has a rectangular shape as viewed in plane, and a plate-like second electrolyte portion 141 formed of zirconia ceramic and disposed in the through hole 132h of the second surrounding portion 132 (see FIG. 3). The second electrolyte portion 141 has an electrolyte main surface 143 facing the other side DT2 and an electrolyte main surface 144 facing the one side DT1 (see FIG. 4). The third conductor layer 190 disposed on the other side DT2 (upper side in FIG. 4) of the second composite layer 131 is composed of a rectangular third electrode layer 191 disposed on the electrolyte main surface 143 of the second electrolyte portion 141 and inside the through hole 132$h$, and a belt-like third extending layer 192 extending from the third electrode layer 191 toward the longitudinally rear side DL2 (right side in FIGS. 3 and 4). The fourth conductor layer 195 disposed on the one side DT1 (lower side in FIG. 4) of the second composite layer 131 is composed of a rectangular fourth electrode layer 196 disposed on the electrode main surface 144 of the second electrolyte portion 141 and inside the through hole 132$h$, and a belt-like fourth extending layer 197 extending from the fourth electrode layer 196 toward the longitudinally rear side DL2. In the course of using the sensor element 10, the fourth electrode layer 196 also functions as a reference oxygen chamber into which oxygen is pumped from a measuring chamber SP, described below.

The first composite layer 111 includes a plate-like first surrounding portion 112 formed of an insulating ceramic (alumina ceramic) and having a through hole 112$h$ which extends therethrough in the thickness direction DT and has a rectangular shape as viewed in plane, and a plate-like first electrolyte portion 121 formed of zirconia ceramic and disposed in the through hole 112$h$ of the first surrounding portion 112 to airtightly close the through hole 112$h$ (see FIG. 3). The first surrounding portion 112 has a through hole inner-perimetric-surface 115 which defines the through hole 112$h$ (see FIG. 4).

The first electrolyte portion 121 has an electrolyte main surface 123 facing the other side DT2, an electrolyte main surface 124 facing the one side DT1, and an electrolyte outer-perimetric-surface 125 in contact with the through hole inner-perimetric-surface 115 of the first surrounding portion 112 (see FIG. 4).

A mating surface 115$k$ of the through hole inner-perimetric-surface 115 of the first surrounding portion 112 and a mating surface 125$k$ of the electrolyte outer-perimetric-surface 125 of the first electrolyte portion 121 face each other and are entirely in close contact with each other.

The first conductor layer 150 disposed on the other side DT2 of the first composite layer 111 is composed of a rectangular first electrode layer 151 disposed on the electrolyte main surface 123 of the first electrolyte portion 121 and inside the through hole 112$h$ of the first surrounding portion 112, and a belt-like first extending layer 152 extending from the first electrode layer 151 toward the longitudinally rear side DL2 (right side in FIGS. 3 and 4).

The second conductor layer 155 disposed on the one side DT1 of the first composite layer 111 is composed of a rectangular second electrode layer 156 disposed on the electrolyte main surface 124 of the first electrolyte portion 121 and inside the through hole 112$h$, and a belt-like second extending layer 157 extending from the second electrode layer 156 toward the longitudinally rear side DL2.

The insulating layer 170 has a rectangular through hole 170$h$ extending therethrough and being sandwiched between the through hole 112$h$ of the first composite layer 111 and the through hole 132$h$ of the second composite layer 131. The through hole 170$h$ is surrounded by the first composite layer 111 (first electrolyte portion 121) and the second composite layer 131 (second electrolyte portion 141) in addition to the insulating layer 170, thereby defining the hollow measuring chamber SP (see FIG. 4). The insulating layer 170 is composed of a body portion 171 formed of dense alumina, and two porous portions 172 formed of porous ceramic, disposed at respective sides of the through hole 170$h$ extending along the longitudinal direction DL, and exposed to the exterior of the gas sensor element 10 (see FIG. 3). The porous portions 172 are diffusion controlling layers for controlling introduction of the gas to be measured into the measuring chamber SP from outside the gas sensor element 10 at a predetermined flow rate.

The protection layer 160 is laminated on the other side DT2 of the first composite layer 111 and covers the first conductor layer 150. The protection layer 160 is composed of a porous portion 162 which covers the first electrode layer 151 and the first electrolyte portion 121, and a protection portion 161 which surrounds the porous portion 162 and overlies the first surrounding portion 112 to protect the first surrounding portion 112 (see FIG. 3).

As shown in FIG. 3, the protection portion 161 has the three sensor pads 16, 17, and 18 disposed on a first main surface 160$a$ (the aforementioned first element main surface 10$a$) facing the other side DT2 and located toward the longitudinally rear side DL2. The sensor pad 16 electrically communicates with a rear end portion 197$e$ located toward the rear side DL2 of the fourth extending layer 197 through hole conductors BC formed in through holes 161$m$, 112$m$, 171$m$, and 132$m$ extending through the protection layer 160, the first composite layer 111, the insulating layer 170, and the second composite layer 131, respectively. The sensor pad 17 electrically communicates with a rear end portion 152$e$ located toward the rear side DL2 of the first extending layer 152 through the through hole conductor BC formed in a through hole 161$n$ extending through the protection layer 160 (see FIG. 3). Furthermore, the sensor pad 18 electrically communicates with a rear end portion 157$e$ of the second extending layer 157 and a rear end portion 192$e$ of the third extending layer 192 through the through hole conductors BC formed in through holes 161$p$, 112$p$, and 171$p$ extending through the protection layer 160, the first composite layer 111, and the insulating layer 170, respectively (see FIG. 3).

The heater layer 180 includes two plate-like insulating layers 182 and 183 formed of alumina and located on the one side DT1 with respect to the first composite layer 111, and the heater 181 formed primarily of Pt and embedded between the insulating layers 182 and 183 (see FIGS. 3 and 4). The heater 181 is composed of a meandering heat-generating portion 181$d$ and a first lead portion 181$b$ and a second lead portion 181$c$ connected to the respective opposite ends of the heat-generating portion 181$d$ and extending rectilinearly. A rear end portion 181$e$ of the first lead portion 181$b$ electrically communicates with the heater pad 14 through the through hole conductor BC formed in a through hole 183$m$ extending through the insulating layer 183, and a rear end portion 181$f$ of the second lead portion 181$c$ electrically communicates with the heater pad 15 through the through hole conductor BC formed in a through hole 183$n$ extending through the insulating layer 183 (see FIG. 3). By supplying electric current to the heater 181, the first electrolyte portion 121 of the first composite layer 111 and the second electrolyte portion 141 of the second composite layer 131 are heated and activated, whereby the gas sensor element 10 actively functions.

In the gas sensor element 10 according to the present embodiment, oxygen is supplied beforehand to the fourth electrode layer 196 to form a reference oxygen chamber. Under this condition, the direction and magnitude of current flowing between the first electrode layer 151 and the second electrode layer 156 between which the first electrolyte portion 121 is sandwiched are adjusted such that the first electrolyte portion 121 pumps out oxygen from the measuring chamber SP to the porous portion 162 or pumps oxygen into the measuring chamber SP from the porous portion 162 in order to establish a predetermined potential difference between the third electrode layer 191 and the fourth electrode layer 196 between which the second electrolyte portion 141 is sandwiched (in order to establish a fixed oxygen concentration in the measuring chamber SP). Since the magnitude of current flowing between the first electrode layer 151 and the second electrode layer 156 is proportional to the oxygen concentration of gas to be measured which flows into the measuring chamber SP through the porous portions 172, the oxygen concentration of gas to be measured can be detected from the magnitude of current.

Meanwhile, the gas sensor element 10 of the present embodiment has the following features with respect to the first composite layer 111. The mutually facing mating surfaces 115$k$ and 125$k$ of the electrolyte outer-perimetric-surface 125 of the first electrolyte portion 121 and the through hole inner-perimetric-surface 115 of the first surrounding portion 112, respectively, are sloped toward the exterior of the first electrolyte portion 121 while moving toward the one side DT1 (lower side in FIG. 4). Also, as shown in FIG. 4, in the first electrolyte portion 121 of the present embodiment, an angle θ between an electrolyte main surface 124 located toward the one side DT1 and the mating surface (slope) 125$k$ of the electrolyte outer-perimetric-surface 125 is 70°.

Furthermore, as mentioned above, the mating surface 115$k$ of the through hole inner-perimetric-surface 115 of the first surrounding portion 112 and the mating surface 125$k$ of the electrolyte outer-perimetric-surface 125 of the first electrolyte portion 121 face each other and are entirely in close contact with each other with no gap formed therebetween (see FIG. 3).

The first electrolyte portion 121 is formed by firing an electrolyte sheet member 221 (described below) whose sheet member outer-perimetric-surface 225 (described below) is sloped similarly to the above-mentioned electrolyte outer-perimetric-surface 125. The first surrounding portion 112 is formed by firing an insulating paste layer 212 (described below) in wet contact with the sheet member outer-perimetric-surface 225 of the electrolyte sheet member 221.

As mentioned above, the gas sensor element 10 according to the present embodiment is configured such that the mating surfaces 125$k$ and 115$k$ of the electrolyte outer-perimetric-surface 125 and the through hole inner-perimetric-surface 115 are sloped toward the exterior of the first electrolyte portion 121 while moving toward the one side DT1. Thus, the length of contact in the thickness direction DT between the mating surface 125$k$ of the first electrode portion 121 and the mating surface 115$k$ of the first surrounding portion 112 can be increased. Furthermore, the mating surfaces 115$k$ and 125$k$ of the through hole inner-perimetric-surface 115 and the electrode outer-perimetric-surface 125, respectively, are entirely in close contact with each other. Thus, the formation of a communication gap between the opposite main surfaces 123 and 124 of the first electrolyte portion 121 can be restrained between the first electrolyte portion 121 and the first surrounding portion 112, whereby the gas sensor element 10 can be free from deterioration in accuracy, which could otherwise result from flow of gas through the gap. Therefore, the gas sensor element 10 can provide high reliability.

The first electrolyte portion 121 is formed by firing the electrolyte sheet member 221, and the first surrounding portion 112 is formed by firing the insulating paste layer 212. Furthermore, before firing, the insulating paste layer 212 is in contact with the sheet member outer-perimetric-surface 225 of the electrolyte sheet member 221. Thus, since firing is performed while the slope of the sheet member outer-perimetric-surface 225 is maintained, the mating surface 125$k$ of the electrolyte outer-perimetric-surface 125 of the first electrolyte portion 121 can be reliably sloped as mentioned above. Furthermore, the insulating paste layer 212 is in close contact with the sheet member outer-perimetric-surface 225 which is to become the electrolyte outer-perimetric-surface 125. Therefore, the gas sensor element 10 can be configured such that the mating surfaces 125$k$ and 115$k$ of the electrolyte outer-perimetric-surface 125 and the through hole inner-perimetric-surface 115 of the first surrounding portion 112 are entirely in close contact with each other in a reliable manner.

By employing the above-mentioned gas sensor element 10, the gas sensor 1 according to the present embodiment can provide high reliability by restraining a problem resulting from formation of a gap between the first electrolyte portion 121 and the first surrounding portion 112.

Furthermore, in this gas sensor element 10, the heater 181 is disposed on the one side DT1 (lower side in FIG. 3) with respect to the first electrolyte portion 121 having the mating surface 125$k$ (slope) which is sloped such that its position changes outwardly while moving toward the one side DT1. That is, the first electrolyte portion 121 whose sectional area increases while moving toward the one side DT1 can be heated by the heater 181 from the one side DT1 with respect to the first electrolyte portion 121. Thus, heating the first electrolyte portion 121 is facilitated, whereby the first electrolyte portion 121 can more quickly increase in temperature and become activated as compared with the case where the mating surface is oppositely inclined.

Next, a method of manufacturing the gas sensor element 10 of the gas sensor 1 according to the present embodiment will be described with reference to FIGS. 5 to 8. In the present embodiment, a sheet thickness direction DZ indicates the thickness direction of the electrolyte sheet member 221, etc., which are described below.

First, a cutting-out step is performed for cutting out the electrolyte sheet member 221 having the sheet member outer-perimetric-surface 225 which is sloped similarly as is the aforementioned electrolyte outer-perimetric-surface 125, from an electrolyte sheet (green sheet) 221B formed of a solid electrolyte ceramic.

In this cutting-out step, by use of a laser beam LB from a CW laser (specifically, YAG laser), the electrolyte sheet member 221 is cut out from the electrolyte sheet 221B. Specifically, the laser beam LB is perpendicularly directed to a main surface 221X. Then, while being moved in a planar direction (e.g., a first direction DX or a second direction DY in FIG. 5A) of the electrolyte sheet 221B, the laser beam LB is continuously emitted.

Figure 5A:
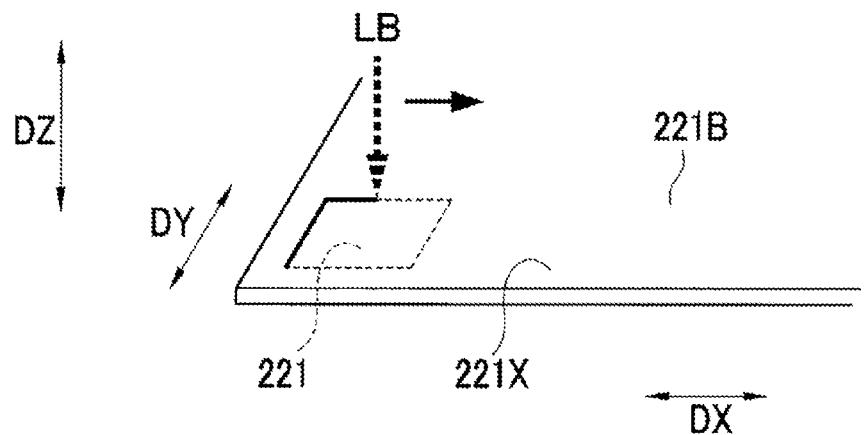
FIG. 5A is an explanatory perspective view illustrating a cutting-out step in manufacture of the gas sensor element according to the embodiment.
Figure 5B:
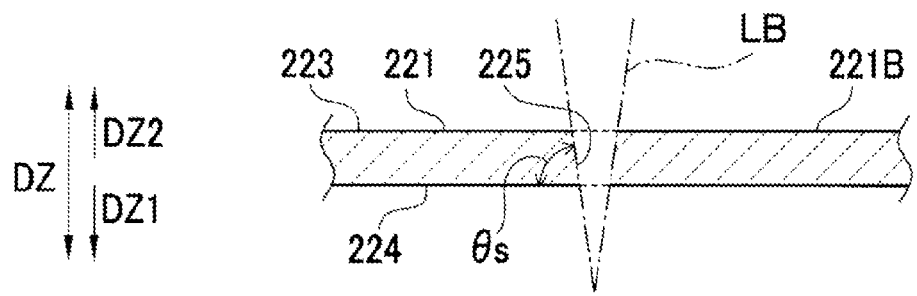
FIG. 5B is an explanatory sectional view illustrating the cutting-out step.

In the present embodiment, since the laser beam LB conically converges, as shown in FIG. 5B, the cut surface (sheet member outer-perimetric-surface 225) of the cut-out electrolyte sheet member 221 is sloped at an angle θs of 70°. In forming a green first composite layer 221 using the electrolyte sheet member 221, the electrolyte sheet member 221 is inverted (placed upside down) from the state of FIG. 5B. In FIG. 5B, the main surface of the electrolyte sheet member 221 facing the other side (upper side) is taken as an electrolyte-sheet main surface 223, and the main surface facing the one side (lower side) and being wider in area than the electrolyte-sheet main surface 223 is taken as an electrolyte-sheet main surface 224.

Next, a green protection layer 260 is prepared. The green protection layer 260 includes a green porous portion 262 which is to become the porous portion 162 after firing, and a green protection portion 261 which surrounds the green porous portion 262 and is to become the protection portion 161 after firing. The green protection layer 260 has the aforementioned through holes 161m, 161n, and 161p provided at the rear side DL2 (right side in FIG. 6) of the green protection portion 261.

Figure 6:
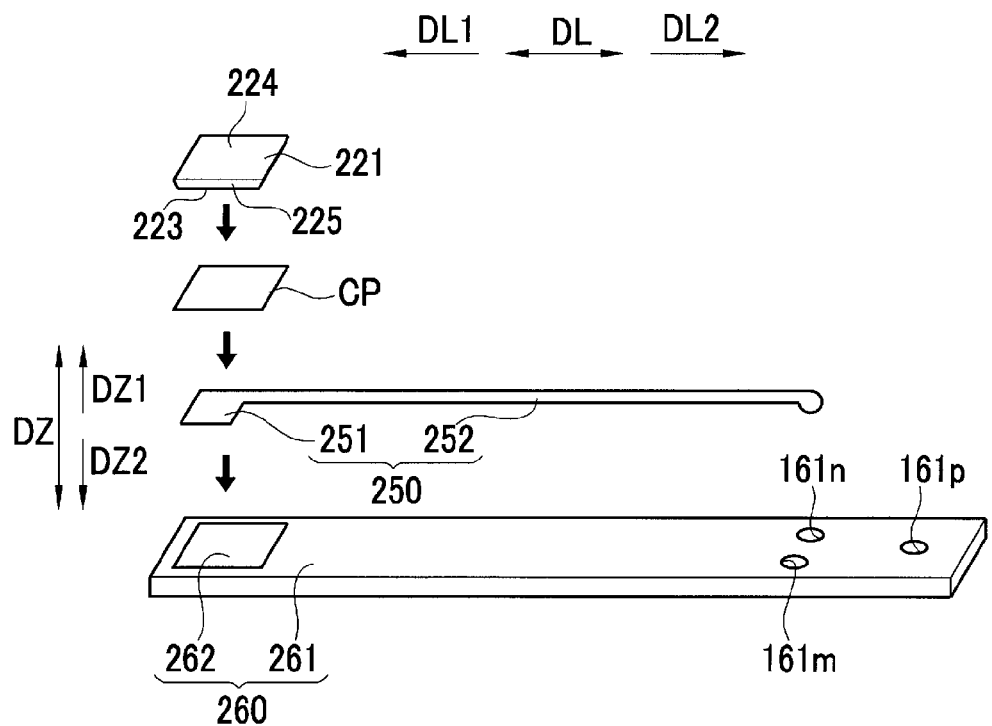
FIG. 6 is an explanatory view illustrating a method of manufacturing the gas sensor element according to the embodiment.

A green first conductor layer 250 was formed on one main surface of the green protection layer 260 (see FIG. 6). Specifically, the green first conductor layer 250 was formed by a known screen printing process such that a green first electrode layer 251 was located on the green porous portion 262 (see FIG. 6). Subsequently, an electrolyte paste layer CP which contained a solid electrolyte ceramic was applied so as to cover the green first electrode layer 251 of the green first conductor layer 250 and the green porous portion 262 of the green protection layer 260; then, the electrolyte sheet member 221 was laminated thereon. The electrolyte paste layer CP contains the same solid electrolyte ceramic as that contained in the electrolyte sheet member 221, and is adapted to bond the electrolyte sheet member 221 to the green first electrode layer 251 and the green porous portion 262. In laminating the electrolyte sheet member 221 on the green porous portion 262, etc., the electrolyte-sheet main surface 223 of the electrolyte sheet member 221 was disposed toward the electrolyte paste layer CP (disposed downward) (see FIG. 6).

Figure 7:
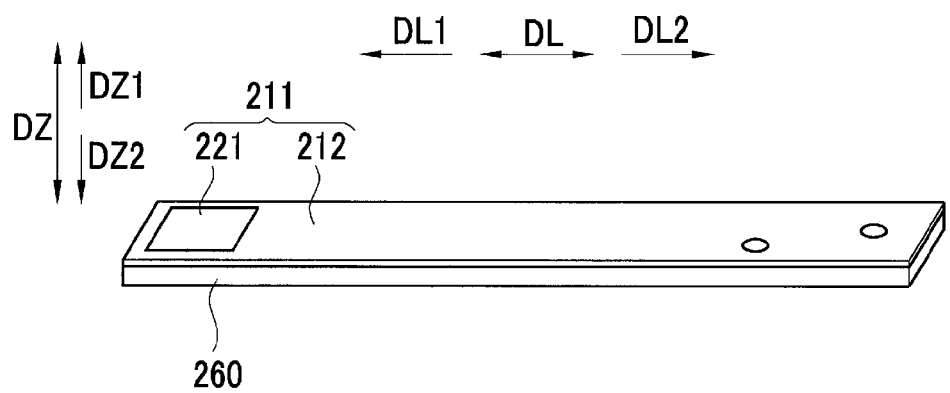
FIG. 7 is an explanatory view illustrating a composite layer forming step in manufacture of the gas sensor element according to the embodiment.

Subsequently, as shown in FIG. 7, the insulating paste layer 212 is disposed around the electrolyte sheet member 221 to perform a composite layer forming step for forming a green first composite layer 211.

Specifically, an insulating paste which contains an insulating ceramic is applied so as to cover the green protection layer 260 and the green first conductor layer 250 and to be in wet contact with the sheet member outer-perimetric-surface 225 of the electrolyte sheet member 221, followed by drying to form the insulating paste layer 212 (see FIG. 7). In applying the insulating paste, since the fluid insulating paste comes in wet contact with the sheet member outer-perimetric-surface 225 which is sloped as mentioned above, even after drying, the insulating paste layer 212 can be reliably brought into close contact with the sheet member outer-perimetric-surface 225 with a large area of contact.

In this manner, the green first composite layer 211 composed of the electrolyte sheet member 221 and the insulating paste layer 212 was formed on the green protection layer 260 (see FIG. 7).

Figure 8:
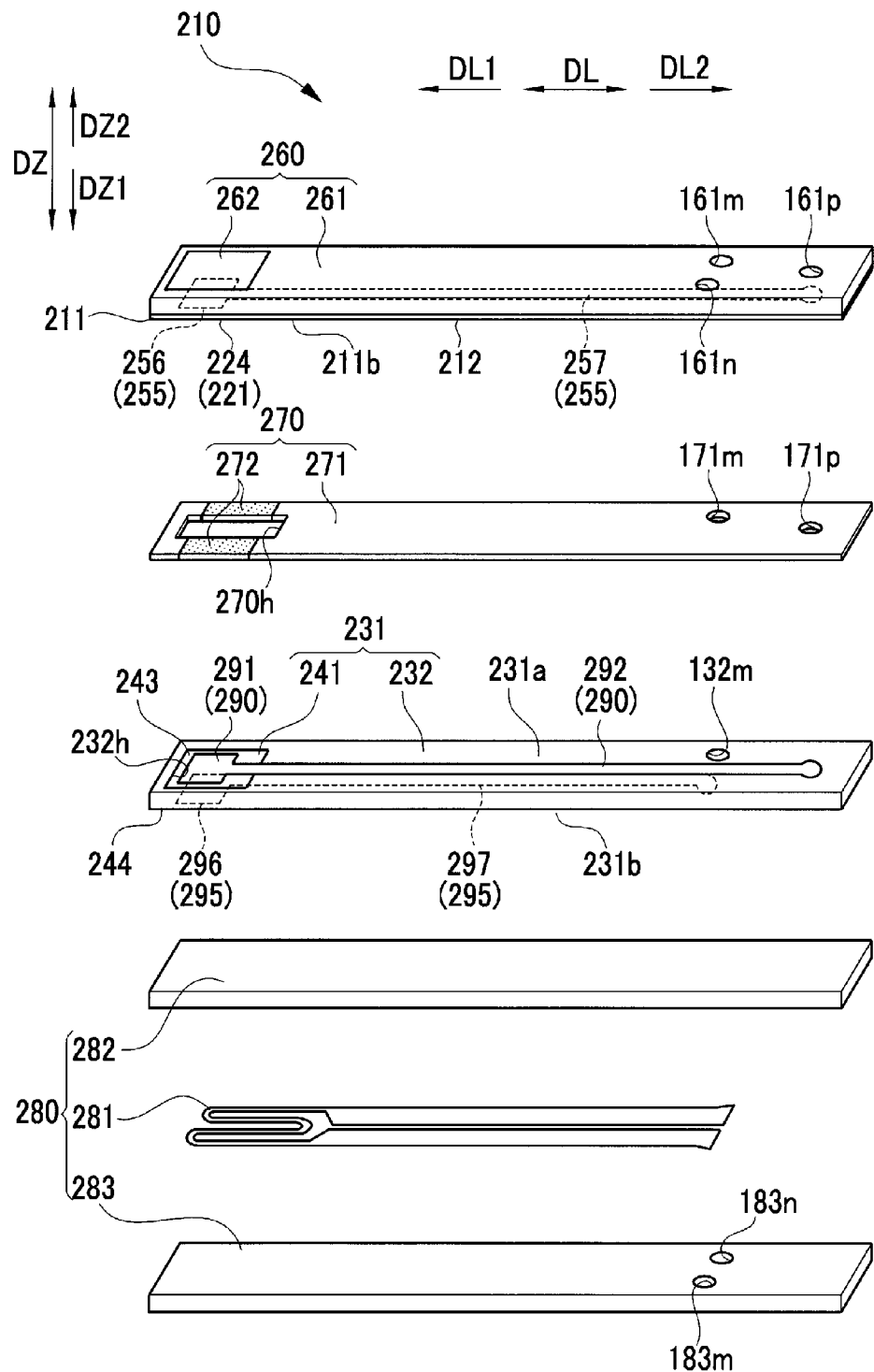
FIG. 8 is an explanatory view illustrating the method of manufacturing the gas sensor element according to the embodiment.

Furthermore, a green second conductor layer 255 was formed on the green first composite layer 211 formed on the green protection layer 260. Specifically, the green second conductor layer 255 was formed by a screen printing process so that a green second electrode layer 256 was located on the electrolyte-sheet main surface 224 of the electrolyte sheet member 221, and a green second extending layer 257 was located on the insulating paste layer 212 (see FIG. 8). In FIG. 8, the green protection layer 260, the green first composite layer 211, the green second conductor layer 255, etc., are inverted (placed upside down) from the state of FIG. 7. Also, in FIG. 8, the vertical direction corresponds to the sheet thickness direction DZ; a side directed upward corresponds to the other side DZ2 with respect to the sheet thickness direction DZ; and a side directed downward corresponds to one side DZ1 with respect to the sheet thickness direction DZ. By contrast, in FIGS. 6 and 7, a side directed upward corresponds to the one side DZ1 with respect to the sheet thickness direction DZ, and a side directed downward corresponds to the other side DZ2 with respect to the sheet thickness direction DZ. Thus, in FIGS. 6 to 8, the green first composite layer 211 has the sheet member outer-perimetric-surface 225 which is sloped toward the exterior of the electrolyte sheet member 221 while moving toward the one side DZ1 with respect to the green first composite layer 211.

Next, using a method known to those of ordinary skill in this field of art, a green second composite layer 231 was formed and configured such that a rectangular plate-like green electrolyte portion 241 formed of the aforementioned electrolyte sheet 221B was disposed in a sheet through hole 232h of a green surrounding portion 232 formed of an insulating green sheet (not shown). The green surrounding portion 232 is to become the second surrounding portion 132 after firing, and the green electrolyte portion 241 is to become the second electrolyte portion 141 after firing.

Subsequently, the through hole 132m was formed in the green surrounding portion 232; then, a green third conductor layer 290 and a green fourth conductor layer 295 were formed by a screen printing process on the respective opposite main surfaces of the green second composite layer 231 (see FIG. 8). Specifically, the green third conductor layer 290 was formed on a first main surface 231a facing the other side DZ2 of the green second composite layer 231 such that a green third electrode layer 291 thereof was located on an electrolyte main surface 243 facing the other side DZ2 of the green electrolyte portion 241 of the above-mentioned green second composite layer 231, and a green third extending layer 292 thereof was located on the green surrounding portion 232. The green fourth conductor layer 295 was formed on a second main surface 231b facing the one side DZ1 of the green second composite layer 231 such that a green fourth electrode layer 296 thereof was located on an electrolyte main surface 244 facing the one side DZ1 of the green electrolyte portion 241, and a green fourth extending layer 297 thereof was located on the green surrounding portion 232.

Furthermore, the through holes 183m and 183n are formed in a green insulating layer 283, and the through holes 171m and 171n are formed in a green body portion 271 of a green insulating layer 270. Also, the green insulating layer 270 is formed having a rectangular through hole 270h and composed of the green body portion 271 which is to become the dense body portion 171 by firing, and green porous portions 272 which are to become the porous portions 172 by firing. The green porous portions 272 partially constitute two respective sides of the through hole 270h extending along the longitudinal direction DL and are exposed laterally (in a direction orthogonal to the longitudinal direction DL and to the sheet thickness direction DZ). Meanwhile, the green insulating layer 270 (the green body portion 271 and the green porous portion 272) can also be formed by a screen printing process on the green first composite layer 211 or on the green second composite layer 231.

Next, as shown in FIG. 8, the green insulating layer 283, the green heater 281, the green insulating layer 282, the green second composite layer 231, the green insulating layer 270, and the green first composite layer 211 laminated with the green protection layer 260 are sequentially laminated together to form a green element 210.

Subsequently, green through hole conductors (not shown) are disposed in the corresponding through holes of the green element 210; furthermore, green pads (not shown) were formed on the green element 210 by a screen printing process so as to close the through holes from outside the green element 210.

Next, a firing step was performed for firing the green element 210 including the green first composite layer 211 (the electrolyte sheet member 221 and the insulating paste layer 212).

The electrolyte sheet member 221 is fired while the slope of the sheet member outer-perimetric-surface 225 is maintained. In this manner, the gas sensor element 10 was manufactured which included the first composite layer 111 composed of the first electrolyte portion 121 and the first surrounding portion 112 having respective slopes (the mutually facing mating surfaces 125k and 115k of the electrolyte outer-perimetric-surface 125 and the through hole inner-perimetric-surface 115, respectively) (see FIGS. 2 and 3).

According to the method of manufacturing the gas sensor element 10 of the present embodiment, in the composite layer forming step, the insulating paste layer 212 is disposed around the electrolyte sheet member 221 so as to be in contact with the sheet member outer-perimetric-surface 225 which is sloped toward the exterior of the electrolyte sheet member 221 while moving toward the one side DZ1 (upward in FIGS. 6 and 7 or downward in FIG. 8) with respect to the sheet thickness direction of the electrolyte sheet 221B. In this manner, the insulating paste layer 212 can be reliably brought in close contact with the sheet member outer-perimetric-surface 225 with a large contact area. Therefore, the gas sensor element 10 can be manufactured which provides high reliability by preventing the formation, after firing, of a gap between the mating surfaces 125 and 115k of the electrolyte outer-perimetric-surface 125 of the first electrolyte portion 121 and the through hole inner-perimetric-surface 115 of the first surrounding portion 112.

Also, in the cutting-out step which precedes the composite layer forming step, the electrolyte sheet member 221 can be reliably formed whose cut surface (sheet member outer-perimetric-surface 225) is sloped as mentioned above. Therefore, the gas sensor element 10 can be manufactured by reliably using the electrolyte sheet member 221 whose sheet member outer-perimetric-surface 225 is sloped as mentioned above.

Modified Embodiment

In the gas sensor 1 of the embodiment mentioned above, as shown in FIG. 4, of the two composite layers 111 and 131, only the first composite layer 111 is configured such that the mating surfaces 115k and 125k of the first electrolyte portion 121 and the first surrounding portion 112 are sloped such that their positions change outwardly while moving toward the one side DT1. That is, in the second composite layer 131, second mating surfaces 135k and 145k of the second electrolyte portion 141 and the second surround portion 132, respectively, are in parallel with the thickness direction DT.

Figure 9:
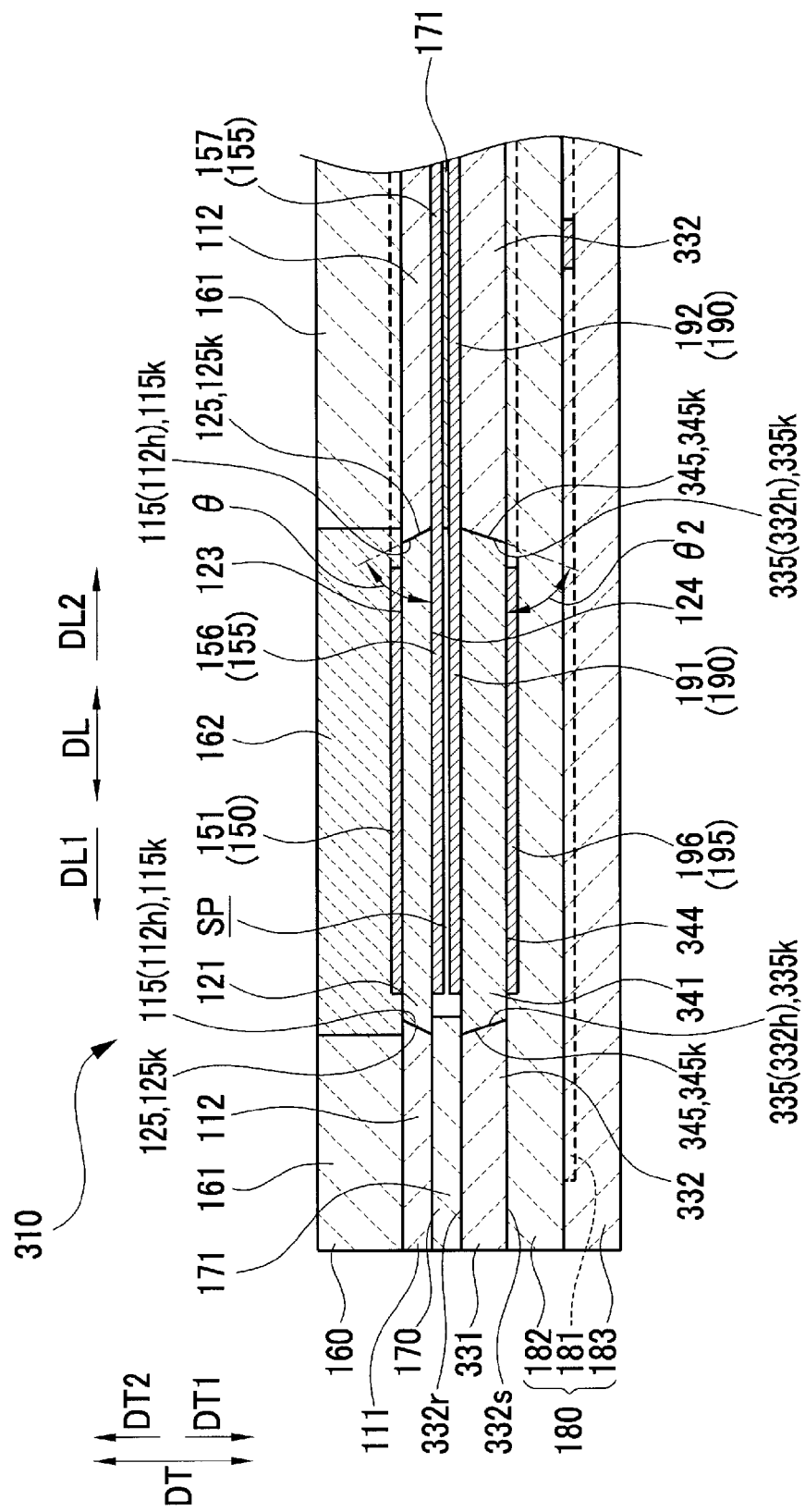
FIG. 9 is an explanatory sectional view illustrating the structure of the gas sensor element according to the modified embodiment.

By contrast, in a gas sensor element 310 of a gas sensor 301 according to the present modified embodiment, as shown in FIG. 9, not only is the first composite layer 111, but also a second composite layer 331 is configured such that second mating surfaces 335k and 345k of a second electrolyte portion 341 and a second surrounding portion 332, respectively, are sloped. Furthermore, in contrast to the first composite layer 111, the second mating surfaces 335k and 345k are sloped such that their positions change inwardly while moving toward the one side DT1. Thus, the present modified embodiment will be described, centering on features different from those of the embodiment. Components similar to those of the embodiment are denoted by like reference numerals, and description thereof is omitted or given in brief.

As mentioned above, the gas sensor element 310 of the gas sensor 301 of the present modified embodiment is configured such that the heater layer 180, the fourth conductor layer 195, the second composite layer 331, the third conductor layer 190, the insulating layer 170, the second conductor layer 155, the first composite layer 111, the first conductor layer 150, and the protection layer 160 are sequentially laminated together from the one side DT1. These layers except the second composite layer 331 are configured similar to those of the gas sensor element 10 of the embodiment.

Similar to the second composite layer 131 of the embodiment, the second composite layer 331 includes a plate-shaped second surrounding portion 332 formed of an insulating ceramic (alumina ceramic) and having a through hole 332h which extends therethrough in the thickness direction DT and has a rectangular shape as viewed in plane, and a plate-like second electrolyte portion 341 formed of zirconia ceramic and disposed in the through hole 332h of the second surrounding portion 332 (see FIG. 3). The second electrolyte portion 341 is disposed in the through hole 332h of the second surrounding portion 332, and a second electrolyte outer-perimetric-surface 345 of the second electrolyte portion 341 is in contact with a second through hole inner-perimetric-surface 335 of the second surrounding portion 332. As understood from FIGS. 3 and 9, the second composite layer 331 is disposed between the first composite layer 111 and the heater 181. The first composite layer 111 and the second composite layer 331 are separated from each other by the insulating layer 170. Thus, the second electrolyte portion 341 of the second composite layer 131 is located away from the first electrolyte portion 121 of the first composite layer 111 to form the measuring chamber SP into which a gas to be measured is introduced.

In the first composite layer 111 of the gas sensor element 10, the mutually facing mating surfaces 115k and 125k of the electrolyte outer-perimetric-surface 125 of the first electrolyte portion 121 and the through hole inner-perimetric-surface 115 of the first surrounding portion 112, respectively, are sloped such that their positions change outwardly while moving toward the one side DT1, and are entirely in close contact with each other.

Furthermore, in the second composite layer 331, the mutually facing second mating surfaces 335k and 345k of the electrolyte outer-perimetric-surface 345 of the second electrolyte portion 341 and the through hole inner-perimetric-surface 335 of the second surrounding portion 332, respectively, are sloped such that their positions change inwardly while moving toward the one side DT1. That is, in the second composite layer 331, the second surrounding portion 332, which has a thermal conductivity that is higher than that of the second electrolyte portion 341, has a greater area on the one side DT1 (i.e., on the heater 181 side) than on the other side DT2.

As shown in FIG. 9, in the second electrolyte portion 341 of the present modified embodiment, an angle θ2 (acute angle) between an electrolyte main surface 344 located toward the one side DT1 and the second mating surface (slope) 345k of the electrolyte outer-perimetric-surface 345 is 70°.

Alumina ceramic (thermal conductivity σs=20 to 30 (W/mK)) used to form the first surrounding portion 112 and the second surrounding portion 332 has a higher thermal conductivity than that of zirconia ceramic (thermal conductivity σp=3 (W/mK)) used to form the first electrolyte portion 121 and the second electrolyte portion 341. That is, in the second composite layer 331, the second surrounding portion 332 having a relatively high thermal conductivity has a greater area on the one side DT1 (i.e., on the heater 181 side) than on the other side DT2.

In the gas sensor elements 10 and 310 (see FIGS. 4 and 9) of the embodiment and the modified embodiment described above, the second composite layer 131 (331) intervenes between the first composite layer 111 and the heater 181. Furthermore, the measuring chamber SP, which is a gap, also intervenes therebetween. Thus, heat from the heater 181 is less likely to reach the first electrolyte portion 121 of the first composite layer 111 as compared with the second electrolyte portion 141 (341) of the second composite layer 131 (331). Accordingly, the temperature of the first electrolyte portion 121 of the first composite layer 111 is less likely to increase.

Thus, in the gas sensor elements 10 and 310 of the embodiment and the modified embodiment, respectively, as mentioned above, the mating surfaces 115k and 125k are sloped such that their positions change outwardly while moving toward the one side DT1, so as to conduct more heat to the first electrolyte portion 121.

Additionally, in the gas sensor element 310 of the present modified embodiment, in the second composite layer 331, the second mating surfaces 335k and 345k are sloped such that their positions change inwardly while moving toward the one side DT1. Consequently, the second surrounding portion 332 can receive heat generated by the heater 181 in a greater amount from one surface 332s thereof facing the one side DT1 and having a relatively large area as compared with the other surface 332r thereof facing the other side DT2 and can efficiently transfer the heat from the other surface 332r toward the first composite layer 111 through the insulating layer 170. Thus, as compared with the case where the second mating surfaces 135k and 145k are in parallel with the thickness direction as in the case of the embodiment described above or are sloped such that their positions change outwardly while moving toward the one side DT1, the first electrolyte portion 121 of the first composite layer 111 can be more efficiently heated to increase its temperature.

Since the second electrolyte portion 341 is in proximity to the heater 181, the second electrolyte portion 341 can be easily heated to increase its temperature.

The second mating surface 335k of the second through hole inner-perimetric-surface 335 of the second surrounding portion 332 and the second mating surface 345k of the second electrolyte outer-perimetric-surface 345 of the second electrolyte portion 341 face each other and are sloped and are entirely in close contact with each other with no gap formed therebetween (see FIG. 3). Thus, the gas sensor 301 can provide high reliability by restraining a problem resulting from formation of a gap between the second electrolyte portion 341 and the second surrounding portion 332.

Since the second composite layer 331 may be formed by a method similar to that of forming the first composite layer 111 in the embodiment, the method will be briefly described below. First, an electrolyte sheet (green sheet) formed of a solid electrolyte ceramic is irradiated with the conically converging laser beam LB to cut out a second electrolyte sheet member whose cut surface is sloped at an angle θs of 70°. Subsequently, an insulating paste which contains an insulating ceramic is applied around the second electrolyte sheet member so as to be in wet contact with the outer perimetric surface of the second electrolyte sheet member, followed by drying to form the insulating paste layer (see FIG. 7). By employing such application of the insulating paste, since the fluid insulating paste comes into wet contact with the sheet member outer-perimetric-surface 225 which is sloped as mentioned above, even after drying, the insulating paste layer can be reliably brought into close contact with the sheet member outer-perimetric-surface of the electrolyte sheet member with a large contact area.

While the present invention has been described with reference to the embodiment and the modified embodiment, the present invention is not limited thereto, and may be modified as appropriate without departing from the gist of the invention.

In the gas sensor element 10 of the embodiment described above, of two composite ceramic layers (the first composite layer 111 and the second composite layer 131), the first composite layer 111 is configured such that the mating surface 125k of the electrolyte outer-perimetric-surface 125 is sloped such that its position changes outwardly while moving toward the one side DT1. In the modified embodiment, of the two composite ceramic layers (the first composite layer 111 and the second composite layer 331), the first composite layer 111 is configured such that the mating surface 125k of the electrolyte outer-perimetric-surface 125 is sloped such that its position changes outwardly while moving toward the one side DT1, and the second composite layer 331 is configured such that the second mating surface 345k of the second electrolyte outer-perimetric-surface 345 is sloped such that its position changes inwardly while moving toward the one side DT1.

However, the gas sensor element may have the following configurational feature: the first composite layer and the second composite layer are configured such that the electrolyte outer-perimetric-surface and the second electrolyte outer-perimetric-surface are sloped such that their positions change outwardly while moving toward the one side or are sloped such that their positions change inwardly while moving toward the one side. According to this gas sensor element, the length of contact along the thickness direction can be increased between the mating surfaces of the electrolyte portions (the first electrolyte portion and the second electrolyte portion) and the mating surfaces of the surrounding portions (the first surrounding portion and the second surrounding portion). Furthermore, since the mating surfaces of the through hole inner-perimetric-surfaces and the electrolyte outer-perimetric-surfaces are entirely in close contact with each other, the formation of gaps allowing for communication between the opposite main surfaces of the electrolyte portions can be restrained between the electrolyte portions and the surrounding portions.

In the embodiment and the modified embodiment described above, the present invention is applied to a gas sensor element having two composite ceramic layers. However, the present invention may be applied to a gas sensor element having a single composite ceramic layer or to a gas sensor element having three composite ceramic layers. In the case of a gas sensor element having three composite ceramic layers, at least one composite ceramic layer is configured such that an electrolyte portion thereof is sloped as mentioned above.

Furthermore, in the embodiment and the modified embodiment described above, an insulating ceramic (alumina ceramic) is used to form the first and second surrounding portions of the first and second composite layers. However, a mixed ceramic of alumina and zirconia may be used.

Also, in the embodiment described above, the first electrolyte portion (electrolyte portion) 121 and the first surrounding portion (surrounding portion) 112 which constitute the first composite layer (composite ceramic layer) 111 have the same thickness; the entire electrolyte outer-perimetric-surface 125 of the first electrolyte portion 121 serves as the mating surface 125$k$; and the entire through hole inner-perimetric-surface 115 of the first surrounding portion 112 serves as the mating surface 115$k$. However, the following mode may exist: because of a difference in thickness between the electrolyte portion and the surrounding portion or a difference in position along the thickness direction between the electrolyte portion and the surrounding portion, a portion of the electrolyte outer-perimetric-surface serves as a mating surface, and a portion of the through hole inner-perimetric-surface serves as a mating surface.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application claims priority from Japanese Patent Application No. 2014-195520 filed Sep. 25, 2014, Japanese Patent Application No. 2015-123522 filed Jun. 19, 2015 and Japanese Patent Application No. 2015-123853 filed Jun. 19, 2015, the above-noted Application incorporated herein by reference in their entirety.

What is claimed is:

1. A gas sensor element comprising a first composite ceramic layer having a plate-shaped first electrolyte portion and a plate-shaped first surrounding portion, the first electrolyte portion formed of a solid electrolyte ceramic and including a first electrolyte outer-perimetric-surface and the first surrounding portion formed of an insulating ceramic or a mixture of an insulating ceramic and the solid electrolyte ceramic and including a first through hole inner-perimetric-surface,
   wherein the first through hole inner-perimetric-surface defines a through hole which extends through the gas sensor element in a thickness direction, the first electrolyte portion disposed in the through hole;
   wherein the first electrolyte outer-perimetric-surface directly contacts the first through hole inner-perimetric-surface; and
   wherein the entire surface of the first electrolyte outer-perimetric-surface and the entire surface of the through hole inner-perimetric-surface which make direct contact with each other are sloped toward an exterior of the first electrolyte portion, forming mutually facing first mating surfaces, the mutually facing first mating surfaces extending in the thickness direction toward a first surface of the first composite ceramic layer.

2. The gas sensor element as claimed in claim 1, wherein the first electrolyte portion is formed by firing an electrolyte sheet member which contains the solid electrolyte ceramic and whose sheet member outer-perimetric-surface is sloped toward an exterior of the sheet member as it approaches the one side with respect to a sheet thickness direction, and
   the first surrounding portion is formed by firing a layer of ceramic paste which is in contact with the sheet member outer-perimetric-surface of the electrolyte sheet member and contains the insulating ceramic or a mixture of the insulating ceramic and the solid electrolyte ceramic.

3. The gas sensor element as claimed in claim 1, further comprising a heater located on a surface side of the gas sensor and adapted to heat the first electrolyte portion.

4. The gas sensor element as claimed in claim 3, further comprising a second composite ceramic layer disposed between the first composite ceramic layer and the heater,
   the second composite ceramic layer having a plate-shaped second electrolyte portion and a plate-shaped second surrounding portion, the second electrolyte portion formed of the solid electrolyte ceramic and including a second electrolyte outer-perimetric-surface and the second surrounding portion formed of the insulating ceramic or a mixture of an insulating ceramic and the solid electrolyte ceramic and including a second through hole inner-perimetric-surface, the second surrounding portion has a higher thermal conductivity than the second electrolyte portion;
   wherein the second through hole inner-perimetric surface defines a second through hole which extends through the gas sensor element in the thickness direction, the second electrolyte portion disposed in the second through hole;
   wherein the second electrolyte outer-perimetric-surface directly contacts the second through hole inner-perimetric-surface;
   wherein the second electrolyte portion is separated from the first electrolyte portion to form a measuring chamber therebetween into which a gas to be measured is introduced; and
   wherein the surface of the second electrolyte outer-perimetric-surface and the surface of the second through hole inner-perimetric-surface which make direct contact with each other are sloped toward an interior of the second electrolyte portion, forming mutually facing second mating surfaces, the mutually facing second mating surfaces extending in the thickness direction toward a first surface of the second composite layer.

5. A gas sensor comprising the gas sensor element as claimed in claim 1.

6. A method of manufacturing a gas sensor element, the gas sensor element comprising a first composite ceramic layer having a plate-shaped first electrolyte portion and a plate-shaped first surrounding portion, the first electrolyte portion formed of a solid electrolyte ceramic and including a first electrolyte outer-perimetric-surface and the first surrounding portion formed of an insulating ceramic or a mixture of an insulating ceramic and the solid electrolyte ceramic and including a first through hole inner-perimetric-surface,
   wherein the first through hole inner-perimetric-surface defines a through hole which extends through the gas sensor element in a thickness direction, the first electrolyte portion disposed in the through hole;
   wherein the first electrolyte outer-perimetric-surface directly contacts the first through hole inner-perimetric-surface; and
   wherein the entire surface of the first electrolyte outer-perimetric-surface and the entire surface of the through hole inner-perimetric-surface which make direct contact with each other are sloped toward an exterior of the first electrolyte portion, forming mutually facing first mating surfaces, the mutually facing first mating surfaces extending in the thickness direction toward a first surface of the first composite ceramic layer,
   the method comprising:
   a composite layer forming step of forming a green composite ceramic layer by disposing a layer of ceramic paste which contains the insulating ceramic or a mixture of the insulating ceramic and the solid electrolyte ceramic, around an electrolyte sheet member formed of a green sheet which contains the solid electrolyte ceramic and having a sheet member outer-perimetric-surface, in such a manner that the layer of ceramic paste comes into contact with the sheet member outer-perimetric-surface, followed by drying, the sheet member outer-perimetric-surface being sloped toward an exterior of the sheet member as it approaches one side with respect to a sheet thickness direction; and a firing step of firing the green composite ceramic layer to form the first composite ceramic layer having the first electrolyte portion and the first surrounding portion.

7. The method of manufacturing a gas sensor element as claimed in claim 6, further comprising a cutting-out step of cutting out, prior to the composite layer forming step, the electrolyte sheet member from the green sheet by directing a conically converging laser beam from a CW laser onto the green sheet and moving the laser beam in a planar direction of the green sheet.

* * * * *